US00PP10626P

United States Patent [19]

Egger

[11] Patent Number: Plant 10,626

[45] Date of Patent: Sep. 29, 1998

[54] LONGIFLORUM ×ASIATIC HYBRID LILY PLANT NAMED 'CEB CHARM'

[75] Inventor: Donald L. Egger, Wilsonville, Oreg.

[73] Assignee: Cebeco Lilies, Inc., Aurora, Oreg.

[21] Appl. No.: 787,622

[22] Filed: Jan. 23, 1997

[51] Int. Cl.[6] ..... A01H 5/00

[52] U.S. Cl. ..... Plt./87.4

[58] Field of Search ..... Plt./87.4

*Primary Examiner*—James R. Feyrer

*Assistant Examiner*—Kent L. Bell

*Attorney, Agent, or Firm*—Klarquist Sparkman Campbell Leigh & Whinston, LLP

[57] ABSTRACT

A new and distinct lily hybrid having upright, large, spotted, orange pink flowers on tall, strong stems excellent for cut flower production.

2 Drawing Sheets

BACKGROUND OF THE INVENTION

The present invention relates to a new and distinct cultivar of lily hybrid referred to commercially as a Longiflorum-Asiatic lily hybrid and named 'Ceb Charm'.

This invention was developed by controlled breeding using 79–674, a proprietary non-released seedling as the seed parent, and PAM#2, another proprietary non- released plant as the pollen parent.

The Longiflorum-Asiatic cross is relatively new to the trade. This type of cross was originally made to create colored *Lilium longiflorum* hybrids. Instead, due to the difficulty in crossing back to *L. longiflorum*, the plants that were developed had to be crossed with Asiatic lilies. As such, the results look more like Asiatic lilies. The resulting hybrids have several advantages over an Asiatic lily: (1) often larger flowers; (2) often larger, waxier leaves; (3) hybrid vigor; (4) lower susceptibility to scorch; (5) excellent flower texture and substance; (6) often more virus resistance; (7) new and clearer colors; (8)often stronger, sturdier stems.

This invention has not been observed under all possible environmental conditions. The phenoytpe may vary significantly with variations in environment such as temperature, light intesity and day length, without, however, any variation in genotype.

The following traits have been repeatedly observed and are determined to be the basic characteristics of this invention which in combination distinguish this lily as a new and distinct cultivar: (1) large, upright flowers of an unusual orange pink color and numerous, distinctive maroon spots; (2) the stigma, style, and filaments are all a similar orange pink color; (3) large, soft orange pink buds; (4) tall, strong stems excellent for cut flowers. Bulbs of this plant may be precooled and forced out of season for very uniform cut flower production.

To the breeder's knowledge, there are no other Longiflorum-Asiatic lily hybrids with this color flower suitable for cut flower forcing on the markert.

Asexual reproduction of this new variety has been accomplished at Cebeco Lilies, Inc., Aurora, Oreg. by scaling and tissue culture. The resulting plants have shown that the abovementioned unique features are stable and reproduce true to type in each successive propagation.

BRIEF DESCRIPTION OF THE DRAWINGS

FIG. 1 is a photograph showing the 'Ceb Charm' lily.

FIG. 2 is a close-up photograph which illustrates in greater detail a single flower of the new plant.

The photographs of the drawing were taken in July 1995 in a studio and illustrate the typical flower and foliage form, with color as true as reasonably possible in this type of color photograph.

DETAILED DESCRIPTION

The following is a detailed description of the invention based on plants produced in accordance with generally accepted commercial practices at the Cebeco Lilies, Inc. research station in Aurora, Oreg. In July 1995. Color references are made to The Royal Horticultural Society Colour Chart, except where the context indicates a term having its ordinary dictionary meaning.

The Plant

Origin: Seedling.

Parentage:

*Seed parent.*—79-674.

*Pollen parent.*—PAM #2.

Commercial classification: Upright Longiflorum-Asiatic hybrid, cut flower type.

Classification: Division VIII, according to the Horticultural Classification of Lilies by The Royal Horticultural Society of London.

Form: Single erect stem bearing terminal cluster of flowers.

Stem color: Yellow green 144A mottled with Greyed-Purple 187A.

Height: About 105 cm. from the top of the soil to the top of the flowers from bulbs of 12 cm. in circumference.

Internodes: 2–10 mm. long.

Growth habit: Vigorous, upright and rigid.

Foliage:

*Arrangement.*—Spiral.

*Quantity.*—Dense.

*Leaf size.*—Variable. To about 14 cm. long and about 15 mm. wide.

*Leaf shape.*—Lanceolate.

*Texture.*—Leathery.

*Aspect.*—Glossy.

*Color.*—Medium green on both sides (146A).

Bulbs:

*Size.*—Variable, ranging to about 12–14 cm. in circumference as used commercially.

*Color.*—White.

The bud

Size: Large, to about 8.5 cm. long and 26mm. wide just prior to opening.

Shape: Ovoid with an obtuse tip. Covered in short, sparse white hairs.

Rate of opening: The mature bud opens slowly in response to light.

Color: Soft orange pink. Greyed red 182 C to Greyed Orange 164C near midrib.

The flower

Blooming habit: Annually, once and early season.

Days to bloom: Flowers approximately 78 days after spring greenhouse planting under typical commercial flower forcing conditions of 15 degrees Celsius night time temperatures.

Inflorescence: About 24 cm. wide and 19 cm. high when four flowers present.

Flower size: Large.

*Diameter.*—About 17 cm.

*Depth.*—About 10 cm.

Borne: In an umbel or modified raceme of 5flowers from bulbs 12–14 cm. in circumference.

Shape: When the flower first opens it is an open cone shape. Later the shape flattens out and the tepals reflex slightly at the tips.

Tepalage:

*Number.*—Six.

*Arrangement.*—Imbricated.

*Shape.*—Ovate.

*Texture.*—Thick, leathery.

*Aspect.*—Satiny.

*Size.*—Length: About 11 cm. Width: Inner tepals—about 60mm. Outer tepals—about 40 mm. Depth of Imbrication: About 15 mm.

*Nectary.*—About 3–3.5 cm. long; white glandular pubescent; channels together.

*Projections.*—Few, terminating in spots.

*Spots.*—Raised; linear (2 mm. long) ; in lines on bottom ⅔ of tepal, Greyed Red 183B.

*Blush.*—Very small, right above the nectary and up the main vein, Yellow Orange 22A.

*Color.*—Topside: Orange pink overall. The very tip is orange red, Orange Red 32B. The top ⅓ and edges are orange pink, Orange-Red 35B-C. Behind the spots on the bottom ⅔ is dull red, Greyed Red 180C. The flower is darker if grown under higher light. Bottomside. Orange pink. Closet to Red Group 35C with 35B at edges.

*Discoloration:*—Lightens with age.

*Fragrance.*—None.

*Lasting quality.*—Excellent.

Pedicle:

*Length.*—Long, usually varies from 6–12 cm.

*Color.*—Yellow green 144A mottled with maroon spots.

*Orientation.*—Ascending upwardly from about 45–90degrees from the horizontal.

The Reproductive Organs

Stamens:

*Number.*—Six, typical of the genus Lilum.

*Anthers before dehiscence.*—Size About 24 mm. Color: Greyed-Orange Group 172 C.

*Filaments.*—Length: About 87 mm. Color: Orange pink, Red-Orange 35C on top half to light orange, Orange 27A on the bottom.

*Pollen.*—Color: Red orange. Greyed-Orange Group 169B.

Pistil:

*Number.*—One.

*Style.*—Length: About 66 mm. Color: Dull orange, Greyed Orange 170C to lighter at base.

*Stigma.*—Color: Dull red orange, Orange Red 34D.

The Fruit

Fertility: Low fertility.

Shape: Ovoid.

Color at maturity: Soft Brown.

I claim:

1. A new and distinct cultivar of Longiflorum-Asiatic hybrid lily plant substantially as herein shown and described.

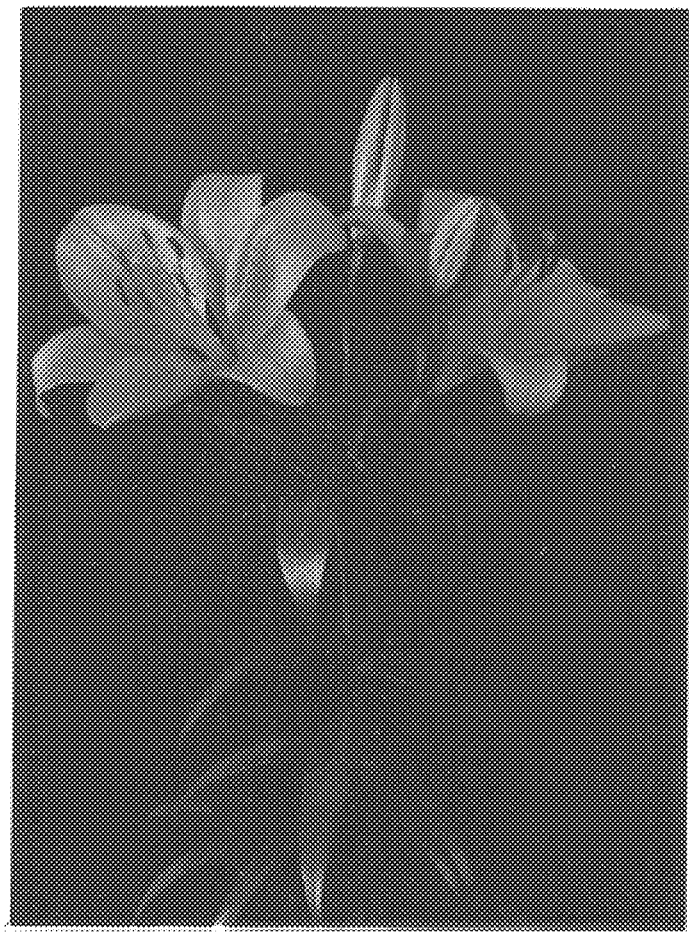

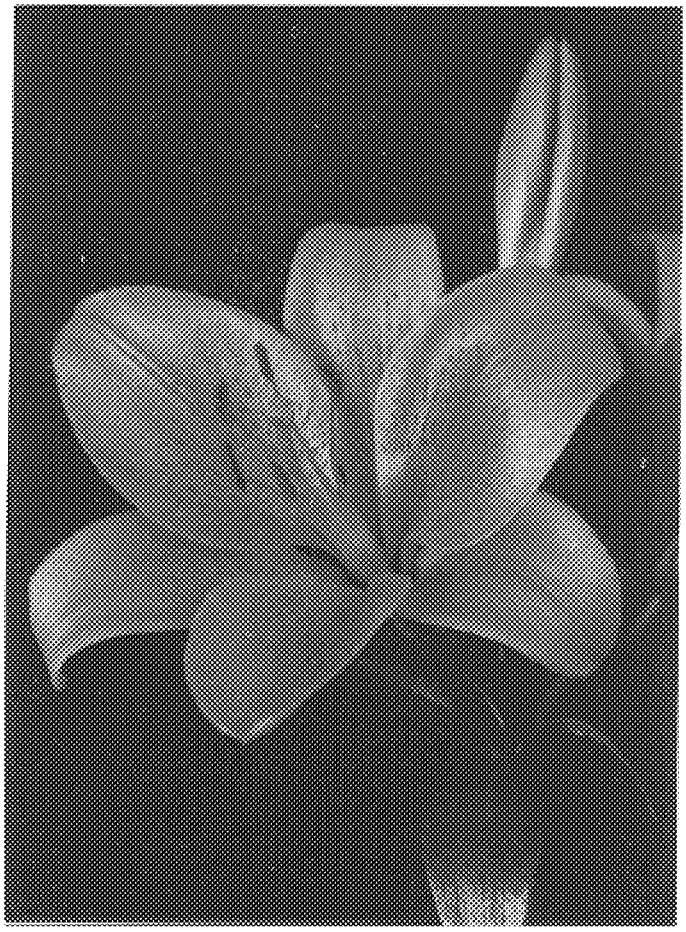

* * * * *